(12) United States Patent
Bashiri et al.

(10) Patent No.: US 7,052,500 B2
(45) Date of Patent: May 30, 2006

(54) EMBOLUS EXTRACTOR

(75) Inventors: Mehran Bashiri, San Carlos, CA (US); Ajitkumar B. Nair, Fremont, CA (US); Pete Phong Pham, Fremont, CA (US); Mark Minh Phung, Union City, CA (US); Lilibeth S. Camins, Fremont, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 128 days.

(21) Appl. No.: 10/045,565

(22) Filed: Oct. 19, 2001

(65) Prior Publication Data

US 2003/0078605 A1   Apr. 24, 2003

(51) Int. Cl.
*A61B 17/24* (2006.01)

(52) U.S. Cl. ..................... 606/113; 606/200
(58) Field of Classification Search ............. 606/200, 606/113, 159, 127, 198
See application file for complete search history.

(56) References Cited

U.S. PATENT DOCUMENTS

| | | |
|---|---|---|
| 3,472,230 A | 10/1969 | Fogarty |
| 3,592,186 A | 7/1971 | Oster |
| 3,683,904 A | 8/1972 | Forster |
| 3,889,657 A | 6/1975 | Baumgarten |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |

(Continued)

FOREIGN PATENT DOCUMENTS

DE          28 21 048          7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Julian W. Woo
(74) *Attorney, Agent, or Firm*—Crompton, Seager & Tufte LLC (57) ABSTRACT

An embolus extractor including elongate shaft having a proximal end and a distal end. The embolus extractor may include first and second struts coupled to the distal end of the shaft. The struts may define a proximally disposed mouth.

25 Claims, 6 Drawing Sheets

U.S. PATENT DOCUMENTS

| | | |
|---|---|---|
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,192,286 A * | 3/1993 | Phan et al. ............... 606/127 |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,482 A * | 7/1994 | Gibbs et al. ............... 606/113 |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazarus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vowerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,398 A | 4/1999 | Wensel et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A * | 8/1999 | Patterson et al. ........... 606/159 |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |

| | | | | | | |
|---|---|---|---|---|---|---|
| 5,989,281 A | 11/1999 | Barbut et al. | EP | 0 472 334 A1 | 2/1992 |
| 5,993,469 A | 11/1999 | McKenzie et al. | EP | 0 472 368 A | 2/1992 |
| 5,997,557 A | 12/1999 | Barbut et al. | EP | 0 472 368 A2 | 2/1992 |
| 6,001,118 A | 12/1999 | Daniel et al. | EP | 0 533 511 A1 | 3/1993 |
| 6,007,557 A | 12/1999 | Ambrisco et al. | EP | 0 655 228 A1 | 11/1994 |
| 6,010,522 A | 1/2000 | Barbut et al. | EP | 0 686 379 A2 | 6/1995 |
| 6,013,085 A | 1/2000 | Howard | EP | 0 696 447 A2 | 2/1996 |
| 6,027,520 A | 2/2000 | Tsugita et al. | EP | 0 737 450 A1 | 10/1996 |
| 6,042,598 A | 3/2000 | Tsugita et al. | EP | 0 743 046 A1 | 11/1996 |
| 6,051,014 A | 4/2000 | Jang | EP | 0 759 287 A1 | 2/1997 |
| 6,051,015 A | 4/2000 | Maahs | EP | 0 771 549 A2 | 5/1997 |
| 6,053,932 A | 4/2000 | Daniel et al. | EP | 0 784 988 A1 | 7/1997 |
| 6,059,814 A * | 5/2000 | Ladd ................... 606/200 | EP | 0 820 729 A | 1/1998 |
| 6,066,149 A | 5/2000 | Samson et al. | EP | 0 852 132 A1 | 7/1998 |
| 6,066,158 A | 5/2000 | Engelson et al. | EP | 1 123 688 A | 8/2001 |
| 6,068,645 A | 5/2000 | Tu | EP | 1 127 556 A2 | 8/2001 |
| 6,086,605 A | 7/2000 | Barbut et al. | FR | 2 580 504 | 10/1986 |
| 6,117,154 A | 9/2000 | Barbut et al. | FR | 2 643 250 A1 | 8/1990 |
| 6,129,739 A | 10/2000 | Khosravi | FR | 2 666 980 | 3/1992 |
| 6,136,016 A | 10/2000 | Barbut et al. | FR | 2 694 687 | 8/1992 |
| 6,142,987 A | 11/2000 | Tsugita | FR | 2 768 326 A1 | 3/1999 |
| 6,152,946 A | 11/2000 | Broome et al. | GB | 2 020 557 B | 1/1983 |
| 6,165,200 A | 12/2000 | Tsugita et al. | JP | 8-187294 A | 7/1996 |
| 6,168,579 B1 | 1/2001 | Tsugita | SU | 764684 | 9/1980 |
| 6,171,327 B1 | 1/2001 | Daniel et al. | WO | WO 88/09683 | 12/1988 |
| 6,171,328 B1 | 1/2001 | Addis | WO | WO 92/03097 | 3/1992 |
| 6,179,851 B1 | 1/2001 | Barbut et al. | WO | WO 94/14389 | 7/1994 |
| 6,179,859 B1 | 1/2001 | Bates et al. | WO | WO 94/24946 | 11/1994 |
| 6,179,861 B1 | 1/2001 | Khosravi et al. | WO | WO 96/01591 | 1/1996 |
| 6,203,561 B1 | 3/2001 | Ramee et al. | WO | WO 96/10375 | 4/1996 |
| 6,206,868 B1 | 3/2001 | Parodi | WO | WO 96/19941 | 7/1996 |
| 6,214,026 B1 | 4/2001 | Lepak et al. | WO | WO 96/23441 | 8/1996 |
| 6,221,006 B1 | 4/2001 | Dubrul et al. | WO | WO 96/33677 | 10/1996 |
| 6,224,620 B1 | 5/2001 | Maahs | WO | WO 97/17100 | 5/1997 |
| 6,231,544 B1 | 5/2001 | Tsugita et al. | WO | WO 97/27808 | 8/1997 |
| 6,235,044 B1 | 5/2001 | Root et al. | WO | WO 97/42879 | 11/1997 |
| 6,235,045 B1 | 5/2001 | Barbut et al. | WO | WO 98/02084 | 1/1998 |
| 6,238,412 B1 | 5/2001 | Dubrul et al. | WO | WO 98/02112 | 1/1998 |
| 6,245,087 B1 | 6/2001 | Addis | WO | WO 98/23322 | 6/1998 |
| 6,245,088 B1 | 6/2001 | Lowery | WO | WO 98/33443 | 8/1998 |
| 6,245,089 B1 | 6/2001 | Daniel et al. | WO | WO 98/34673 | 8/1998 |
| 6,258,115 B1 | 7/2001 | Dubrul | WO | WO 98/36786 | 8/1998 |
| 6,264,663 B1 | 7/2001 | Cano | WO | WO 98/38920 | 9/1998 |
| 6,264,672 B1 | 7/2001 | Fisher | WO | WO 98/38929 | 9/1998 |
| 6,270,513 B1 | 8/2001 | Tsugita et al. | WO | WO 98/39046 | 9/1998 |
| 6,277,138 B1 | 8/2001 | Levinson et al. | WO | WO 98/39053 | 9/1998 |
| 6,277,139 B1 | 8/2001 | Levinson et al. | WO | WO 98/46297 | 10/1998 |
| 6,280,413 B1 | 8/2001 | Clark et al. | WO | WO 98/47447 | 10/1998 |
| 6,287,321 B1 | 9/2001 | Jang | WO | WO 98/49952 | 11/1998 |
| 6,290,710 B1 | 9/2001 | Cryer et al. | WO | WO 98/50103 | 11/1998 |
| 6,309,399 B1 | 10/2001 | Barbut et al. | WO | WO 98/51237 | 11/1998 |
| 6,319,268 B1 | 11/2001 | Ambrisco et al. | WO | WO 98/55175 | 12/1998 |
| 6,344,049 B1 | 2/2002 | Levinson et al. | WO | WO 99/09895 | 3/1999 |
| 6,350,271 B1 | 2/2002 | Kurz et al. | WO | WO 99/22673 | 5/1999 |
| 6,468,291 B1 | 10/2002 | Bates et al. | WO | WO 99/23976 | 5/1999 |
| 6,485,501 B1 | 11/2002 | Green | WO | WO 99/25252 | 5/1999 |
| 6,527,746 B1 * | 3/2003 | Oslund et al. ......... 606/200 | WO | WO 99/30766 | 6/1999 |
| 6,540,722 B1 | 4/2003 | Boyle et al. | WO | 0 934 729 | 8/1999 |
| 6,562,058 B1 | 5/2003 | Seguin et al. | WO | WO 99/40964 | 8/1999 |
| 6,740,061 B1 * | 5/2004 | Oslund et al. ......... 606/200 | WO | WO 99/42059 | 8/1999 |
| | | | WO | WO 99/44510 | 9/1999 |
| FOREIGN PATENT DOCUMENTS | | | WO | WO 99/44542 | 9/1999 |
| | | | WO | WO 99/55236 | 11/1999 |
| DE | 34 17 738 | 11/1985 | WO | WO 99/58068 | 11/1999 |
| DE | 40 30 998 A1 | 10/1990 | WO | WO 00/07521 | 2/2000 |
| DE | 40 39 041 A | 6/1992 | WO | WO 00/07655 | 2/2000 |
| DE | 199 16 162 | 10/2000 | WO | WO 00/09054 | 2/2000 |
| EP | 0 200 688 | 11/1986 | WO | WO 00/16705 | 3/2000 |
| EP | 0 293 605 A1 | 12/1988 | WO | WO 00/49970 | 8/2000 |
| EP | 0 411 118 A1 | 2/1991 | WO | WO 00/53120 | 9/2000 |
| EP | 9 418 677 A | 3/1991 | WO | WO 00/67664 | 11/2000 |
| EP | 0 427 429 A2 | 5/1991 | WO | WO 00/67665 | 11/2000 |
| EP | 0 437 121 B1 | 7/1991 | WO | WO 00/67666 | 11/2000 |

| | | |
|---|---|---|
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/45592 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Artrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

EMBOLUS EXTRACTOR

BACKGROUND OF THE INVENTION

The present invention pertains generally to emboli collection and removal.

Blood thrombus, may form a clot in a patient vasculature. Sometimes such clots are harmlessly dissolved in the blood stream. At other times, however, such clots may lodge in a blood vessel where they can partially or completely occlude the flow of blood. If the partially or completely occluded vessel feeds blood to sensitive tissue such as, the brain, lungs or heart, for example, serious tissue damage may result.

When symptoms of an occlusion are apparent, such as an occlusion resulting in a stroke, immediate action should be taken to reduce or eliminate resultant tissue damage. One approach is to treat a patient with clot dissolving drugs. These drugs, however, do not immediately dissolve the clot and may have harmful side effects. Thus, it may be desirable to physically remove the clot from the patient.

SUMMARY OF THE INVENTION

The present invention pertains to an improved clot or embolus extractor device and method. Various embodiments of the claimed invention are possible, examples of these embodiments will briefly be described herein and in more detail below in the detailed description of the invention. One embodiment of an embolus extractor in accordance with the invention includes two struts coupled to the distal end of an elongate shaft. In a first collapsed position, the struts are generally disposed parallel to the elongate shaft. In a second expanded position, the proximal end of the struts defines a generally circular mouth disposed at approximately 90° to the length of the elongate shaft. The portion of the struts extending distally of the mouth defines a generally tapered, for example, cylindrical body with a conical tip. With such a configuration, an emboli mass, such as a cylindrical thrombus may be contained by the embolus extractor.

One embodiment of an embolus extractor in accordance with the present invention includes an elongate shaft having a proximal end and a distal end. The proximal ends and distal ends of first and second struts are coupled to the shaft and allow rotation of the struts around the shaft. A sleeve may be used to slidably couple the distal ends of the struts to the shaft. A sleeve may also be used to slidably couple the proximal ends of the struts to the shaft. The struts can be disposed in a first position and a second position. In the first position, the distal ends and the proximal ends of the struts are spaced at a first distance. In the second position, the distal ends and the proximal ends of the struts are spaced at a second distance, which is less than the first distance.

In the first position struts can be disposed generally parallel and adjacent to the shaft. In the second position, a proximal portion of the first and second struts can define a generally circular mouth. In the second position, the portion of the struts extending generally distally from the mouth, can define a generally distally tapering body. The proximal portion of the struts forming the mouth can extend from the shaft at 45° to 90° to the length of the shaft. This angle could also be between 60° and 90° or between 80° and 90°.

The struts can include a shaped memory metal, such as NiTi alloy. Additional struts can be added to the embolus extractor to enhance the thrombus containing ability of the embolus extractor. These struts may have a smaller cross sectional diameter than the first and second struts.

In accordance with the present invention, an embolus extractor can be advanced through a patient's vasculature in a first compressed position, distally beyond a clot. The embolus extractor can then be deployed in a second expanded position, then drawn proximally to a second compressed position to capture, contain and remove the thrombus to a larger diameter vessel or from the body.

DETAILED DESCRIPTION

Figure 1:
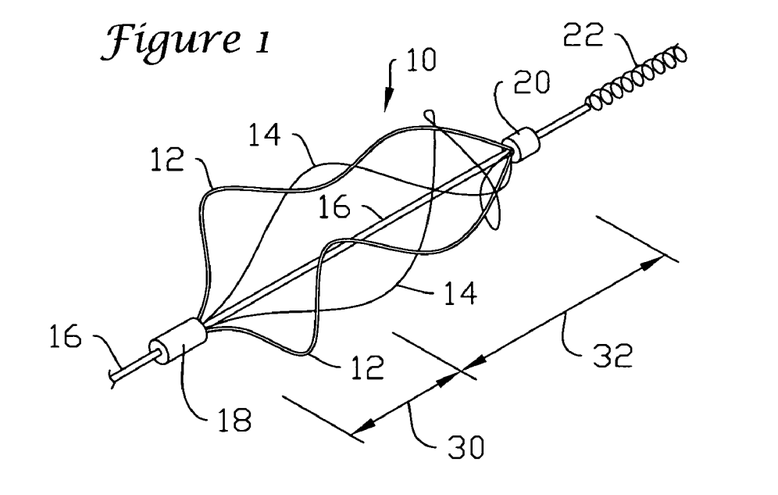
FIG. 1 is a prospective view of a first embodiment of an embolus extractor.

Referring now to the Figures, wherein like referenced numerals refer like elements throughout the several views, FIG. 1 is a perspective view of an embolus extractor 10. Embolus extractor 10 includes first and second primary struts 12 and first and second secondary struts 14 coupled to an elongate shaft 16. Struts 12 and 14 can be coupled to shaft 16 at their proximal ends by a sleeve 18 and at their distal ends by a sleeve 20. A spring tip 22 can be disposed at the distal end of shaft 16. Spring tip 22 can be selectively shaped by a physician to guide embolus extractor 10 into micro vessels and stabilize embolus extractor 10 after deployment.

Struts 12 as shown in FIG. 1 are disposed in an expanded or delivered position. In this position, a proximal portion 30 extends generally perpendicularly to the length of shaft 16 to form a generally circular mouth. A distal portion 32 of struts 12 extending distally of the mouth generally tapers distally to form a distally tapered body having, for example, a generally conical distal shape. Struts 14 transverse the taper body to enhance the clot catching and holding ability of embolus extractor 10. Struts 12 and 14 can be made from various materials including shaped memory metals, such as NiTi alloys. Secondary struts 14 may have a smaller diameter or transverse cross sectional area than primary struts 12.

Elongate shaft 16 can be formed from a material similar to those used for making guide wires, such as plastic polymers, stainless steel, NiTi alloy or other suitable material. Sleeve 18 can be formed from a wire coil. Adhesive, solder or the like may be applied to fixally connect the proximal ends of struts 12 and 14 and sleeve 18 to shaft 16 or the proximal bushing. Sleeve 20 can also be formed from a wire coil. Adhesive, solder or the like can be used to connect struts 12 and 14 to sleeve 20. If struts 12 and 14, are connected to each other, but not fixally connected to shaft 16, sleeve 20 can slide along shaft 16. Both sleeves 18 and 20 can include a radiopaque material. Struts 12 and 14 can also include radiopaque material to visualize their deployed shape.

Figure 2:
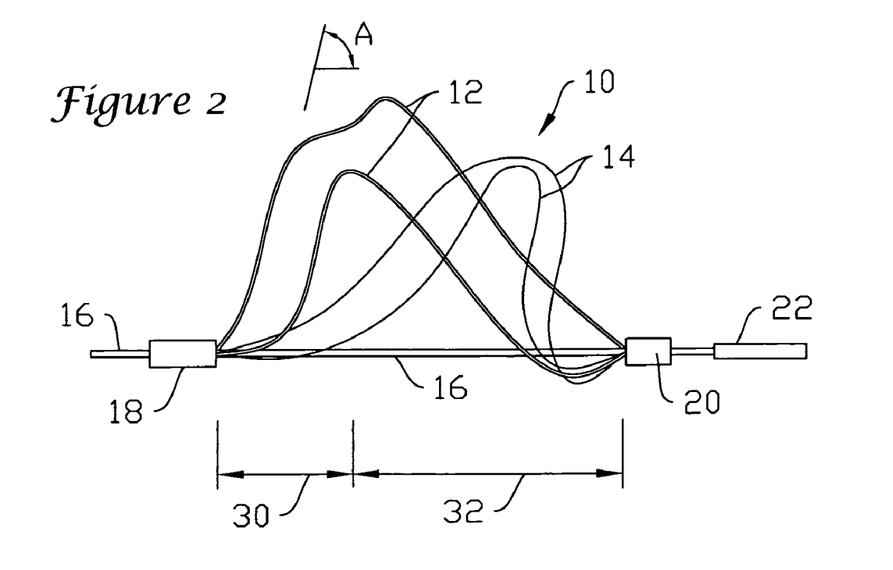
FIG. 2 is a side view of the embolus extractor of FIG. 1.

FIG. 2 is a side view of embolus extractor 10 of FIG. 1. In FIG. 2 embolus extractor 10 is also shown in the expanded or deployed position. Proximal portion 30 of struts 12 defining the mouth is shown disposed at Angle A relative to the length of shaft 16. Angle A can be approximately 90°, between 45° and 90°, between 60° and 90°, or between 80° and 90°. It should be understood that, although Angle A is shown as the angle between the distal end of shaft 16 and proximal portion 30 of struts 12, Angle A can also be the angle between portion 30 of struts 12 and the portion of shaft 16 proximal struts 12. Since each strut 12 defining the generally circular mouth can move independently, the size of the mouth opening can vary. For example, in relatively small vessels, struts 12 can move closer together to create a smaller mouth; whereas in larger vessels, struts 12 can expand to create a larger mouth. If for example, NiTi alloy is used to form struts 12 and 14, struts 12 and 14 can have a preset expanded shape.

The length of shaft 16 and the size of the various elements of embolus extractor 10 can be selected with respect to the location in a patient's vasculature to be accessed. For example, if a patient's cerebral arteries are to be accessed from a femoral approach, the length of shaft 16 should be sized accordingly. The diameter of the generally circular mouth from the proximal portion 30 of struts 12 can be sized to atraumatically engage the wall of the vessel in which it is deployed. The number of primary and secondary struts may be increased or decreased depending on the size of the vessel and the characteristics of the clot.

Figure 3:
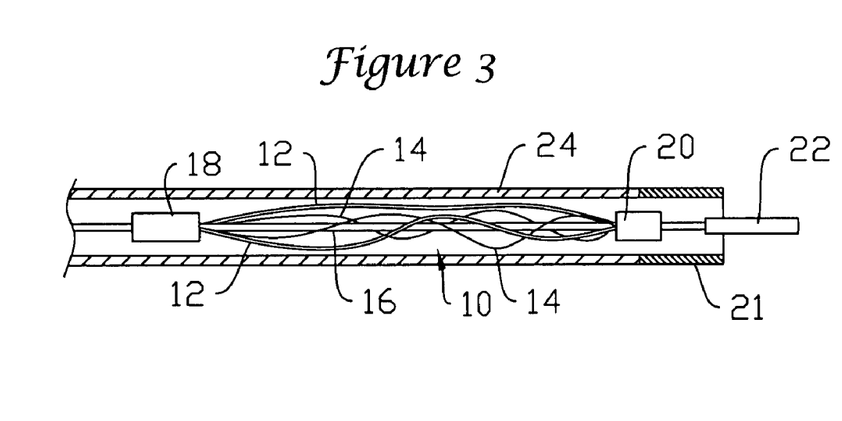
FIG. 3 is a cross sectional view of a micro catheter containing the embolus extractor of FIG. 1.
Figure 4:
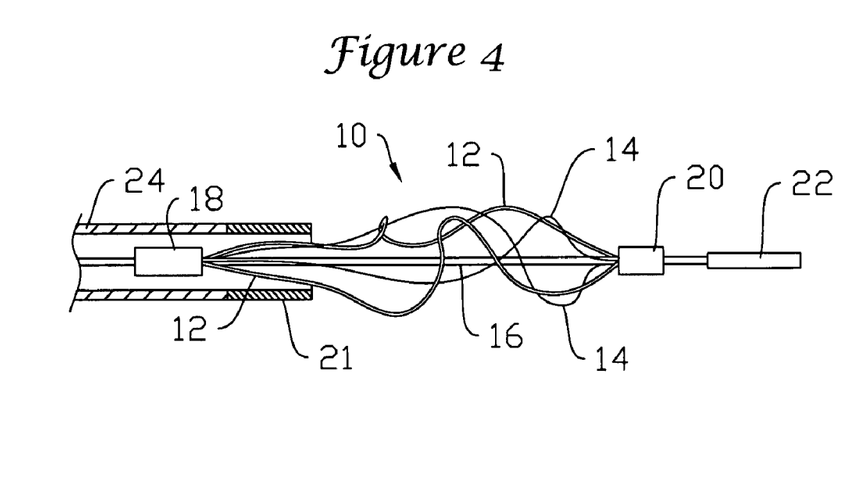
FIG. 4 is a cross sectional view of the micro catheter of FIG. 2 showing the embolus extractor partially disposed from the micro catheter.

FIG. 3 is a cross sectional view of a micro catheter 24 for embolus extractor 10. Micro catheter 24 can have a radiopaque marker tip 21. Tip 21 can be made from, for example, a platinum band or a polymer loaded with a radiopaque material. As shown in FIG. 3, embolus extractor 10 is disposed in a collapsed or delivery position. In this position, sleeve 20 has slide distally along shaft 16 to allow struts 12 and 14 to be compressed within micro catheter 24 and be disposed generally parallel to shaft 16. FIG. 4 is a cross sectional view of micro catheter 24 wherein embolus extractor 10 is disposed in part within micro catheter 24 and in part distally of micro catheter 24. Struts 12 and 14 can be biased to self expand as micro catheter 24 is removed.

Figure 5:
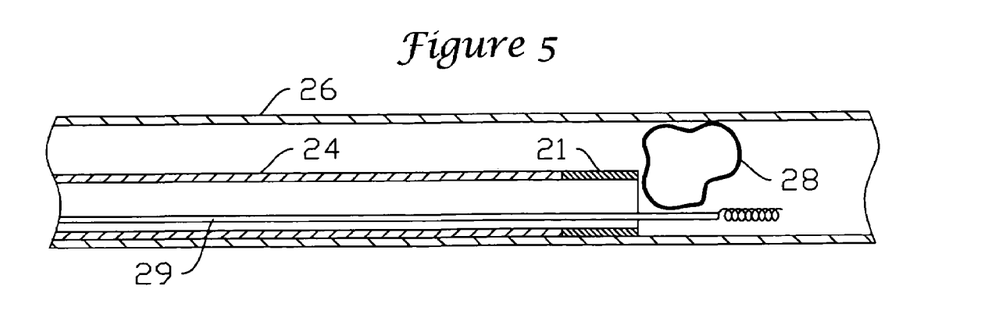
FIG. 5 is a cross sectional view of a vessel including a clot and the embolus extractor of FIG. 1 disposed in a micro catheter positioned proximally of the clot.

FIG. 5 is a cross sectional view of a blood vessel 26 which may be, for example, a cerebral artery. A clot 28, including thrombus is shown occluding vessel 26. A micro guidewire 29 has been advanced distally of clot 28. Micro catheter 24 will then also be advanced distally of clot 28.

Figure 6:
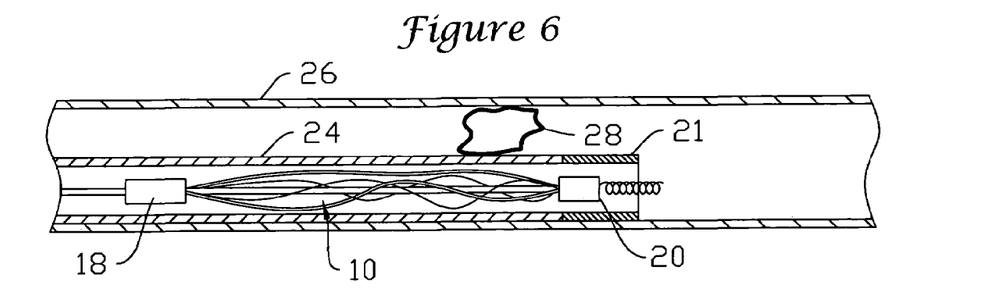
FIG. 6 is a cross sectional view of the vessel of FIG. 5 showing the micro catheter and embolus extractor traversing the clot.

As shown in FIG. 6, micro catheter 24 has been advanced distally of clot 28. Micro guidewire 29 has been removed proximally. Embolus extractor 10 has been placed in micro catheter 24 by an introducer sheath (not shown) at the proximal end of micro catheter 24.

Figure 7:
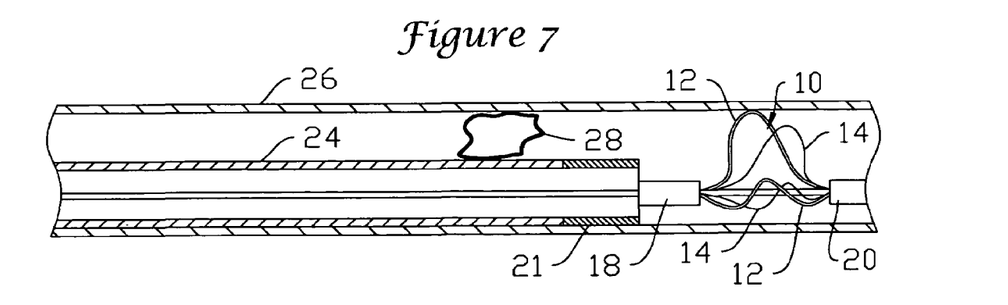
FIG. 7 is a cross sectional view of the vessel of FIG. 5 showing the embolus extractor deployed distally of the clot.

As shown in FIG. 7, once micro catheter 24 and embolus extractor 10 are advanced at least in part distally of clot 28, embolus extractor 10 may be deployed by further advancing embolus extractor 10 relative to micro catheter 24 such that struts 14 in and 12 are allowed to expand. Alternately, micro catheter 24 can be retracted proximally relative to embolus extractor 10 to allow struts 12 and 14 to expand.

Figure 8:
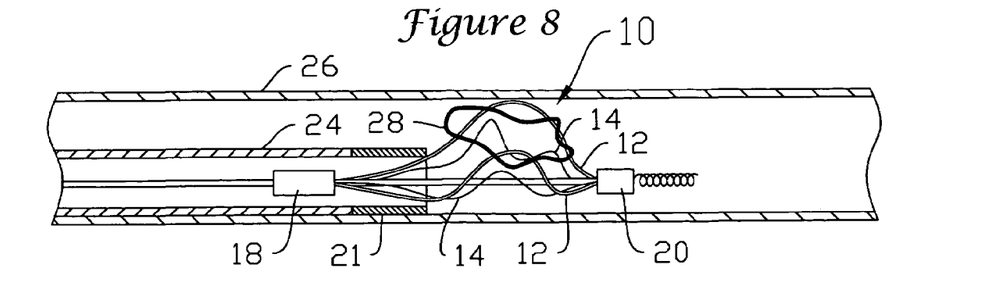
FIG. 8 is a cross sectional view of the vessel of FIG. 5 showing the clot captured by the embolus extractor and the extractor puller locked at the tip of the micro catheter.

As shown in FIG. 8, embolus extractor 10 can then be drawn proximally such that struts 14 and 12 engage and capture clot 28. If struts 12 have been configured such that the proximal mouth engages the wall of vessel 26, the mouth portion can act as a separator to release clot 28 from the vessel wall. After clot 28 has been captured by embolus extractor 10, the profile of struts 12 and 14 can be reduced by placing struts 12 and 14, at least in part, in micro catheter. If sleeve 18 and tip 21 are radiopaqued, the relative distance that embolus extractor 10 is withdrawn within micro catheter 24 can be observed by fluroscopy. Clot 28, embolus extractor 10 and micro catheter 24 can then be removed proximally by way of, for example, a guide catheter (not shown).

Figure 9:
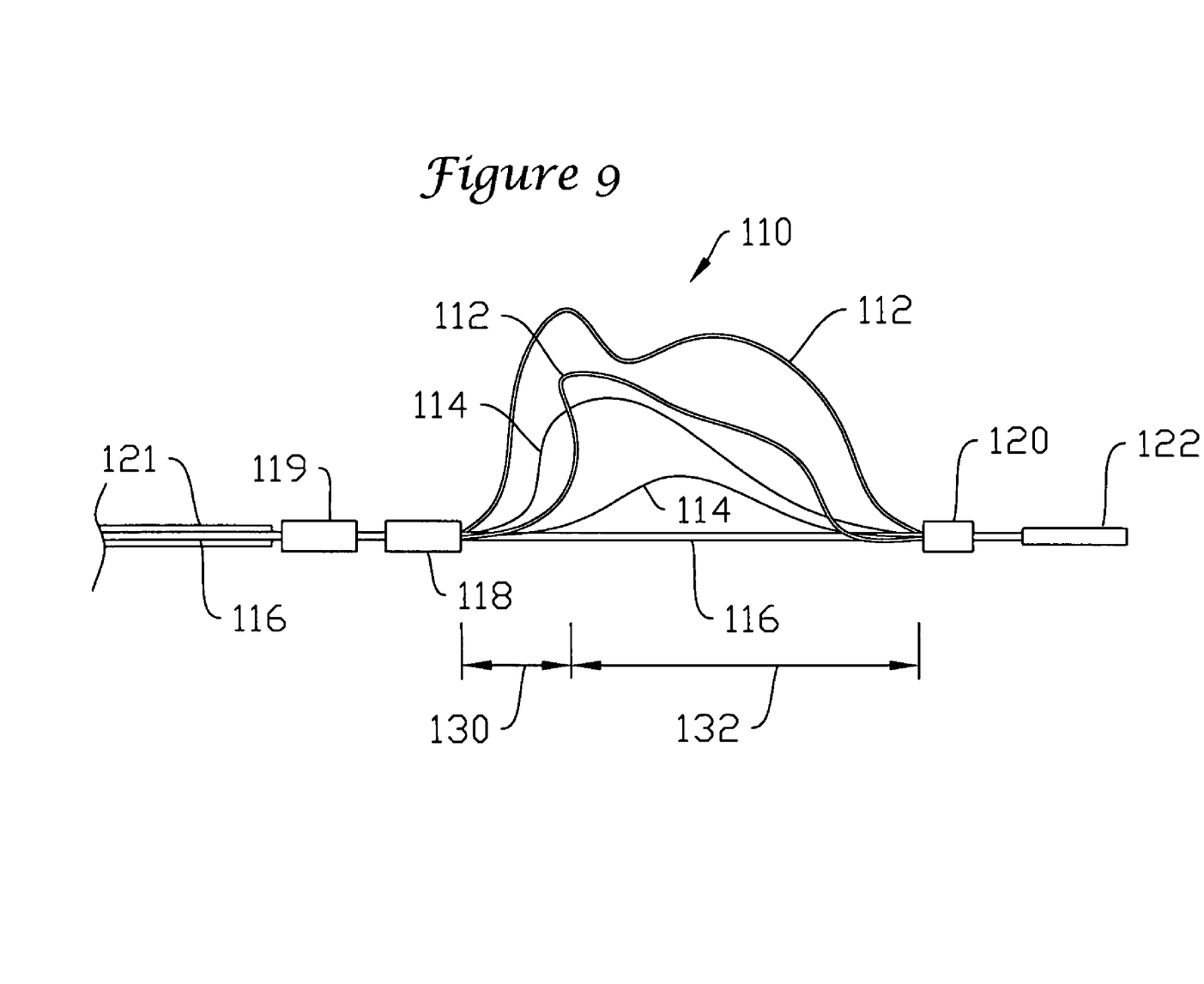
FIG. 9 is a side view of an alternate embodiment of an embolus extractor.

FIG. 9 is a side view of an alternate embodiment of an embolus extractor 110. Embolus extractor 110 can be made from materials, and in an expanded position used in a manner similar to embolus extractor 10. It includes primary struts 112 and secondary struts 114. Primary struts 112 and secondary struts 114 are coupled to elongate shaft 116 at their proximal ends by sleeve 118 and at their distal ends by sleeve 120. In this embodiment, however, both sleeves 120 and 118 are free to slide along shaft 116. Proximal movement, however, can be limited by a stop 119 fastened to elongate shaft 116. Distal movement can be limited by spring tip 122. Like shaft 16, shaft 116 can be formed from a wire.

Shaft 116 can include a polymer coating 121 to improve collapse and repositioning processes of the device. Coating 121 can be polymer tetrafluorine ethylene (PTFE) or other suitable material. Such a coating could be used on any of the shafts described herein.

A proximal end 130 of struts 112 defines a generally circular mouth. A distal portion 132 of struts 112 can define a generally tapered body portion. The mouth portion of embolus extractor 110 can be disposed at an Angle A to shaft 116 as described above with respect to Angle A and embolus extractor 10.

Figure 10:
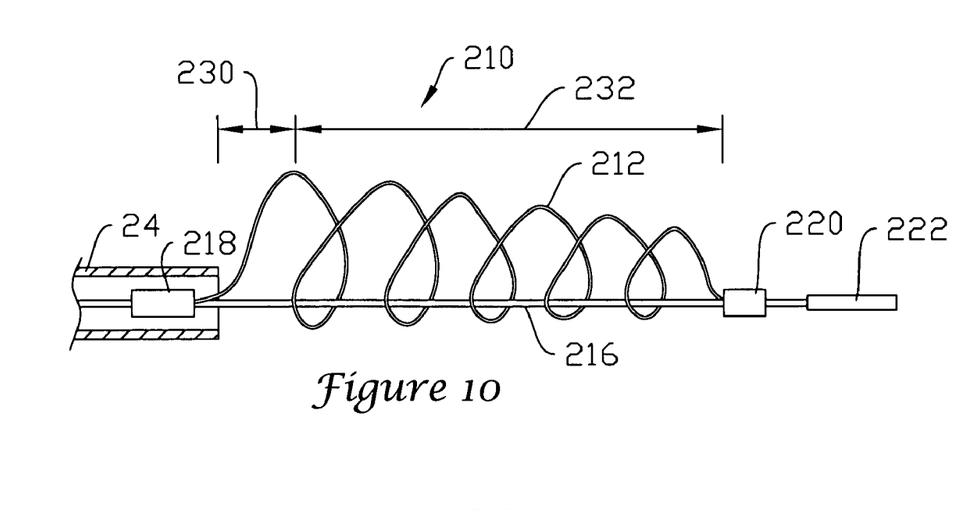
FIG. 10 is a side view of yet an alternate embodiment of an embolus extractor.

FIG. 10 describes yet another embodiment of embolus extractor 210 in an expanded position. Embolus extractor 210 can be made from materials, and used in a way similar to that described above with respect to embolus extractor 10. Embolus extractor 210 includes a generally helical strut 210 coupled to an elongate shaft 216 at its proximal end by sleeve 218, and its distal end by sleeve 220. Sleeve 218 or sleeve 220 can be slidable along shaft 216. If both sleeve 218 and sleeve 220 are slidable along shaft 216, it may be desirable in addition to providing spring tip 222, to provide a proximal stop (not shown) proximal sleeve 218.

A proximal portion 230 of strut 212 can form a generally circular mouth. Distal portion 232 of strut 212 can taper distally to form a tapered body. Portion 230 of strut 212 can be disposed at an Angle A to elongate shaft 216 as described above with respect to Angle A of embolus extractor 10.

Figure 11:
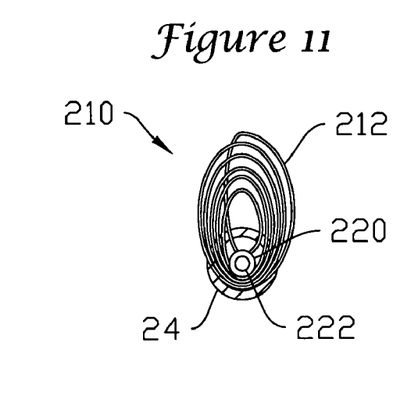
FIG. 11 is a distal end view of the embolus extractor of FIG. 10.

FIG. 11 is a distal end view of embolus extractor 210 of FIG. 10. The generally circular mouth and tapering body of strut 212 can be seen in FIG. 11.

Figure 12:
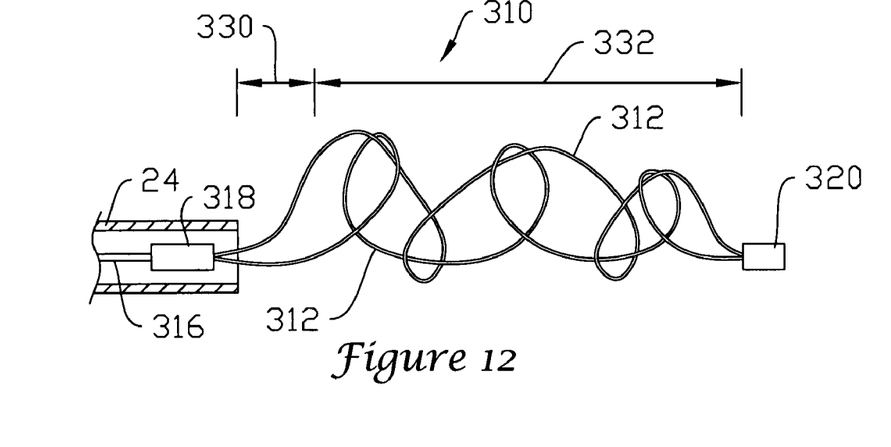
FIG. 12 is a side view of yet an alternate embodiment of an embolus extractor.

FIG. 12 is a side view of yet another alternate embodiment of an embolus extractor 310 in an expanded position. Embolus extractor 310 can be made from materials, and used in a manner similar to that described above with respect to embolus extractor 10. Embolus extractor 310 includes primary struts 312. Struts 312 can be connected at their proximal end by sleeve 318 to an elongate shaft 316. Struts 312 can be coupled together at their distal ends by sleeve 320.

Proximal end 330 of struts 312 can define a generally circular mouth. Distal portion 332 of struts 312 can taper distally to form a distal body portion. Portion 330 of struts 312 can be disposed at an Angle A to elongate shaft 316 as described above with respect to embolus extractor 10.

Figure 13:
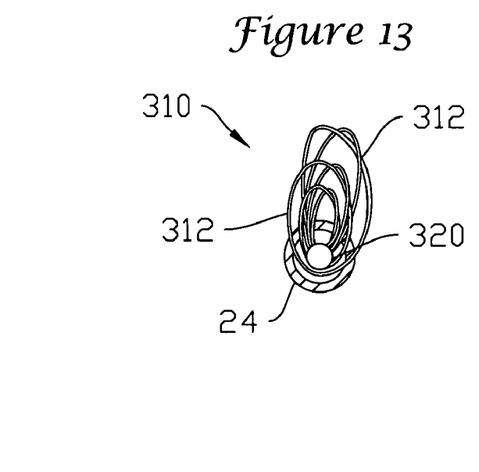
FIG. 13 is a distal end view of the embolus extractor of FIG. 12.

FIG. 13 is a distal end view of embolus extractor 310 of FIG. 12. The generally circular mouth and tapered body portion of embolus extractor 310 can be seen in FIG. 13.

Figure 14:
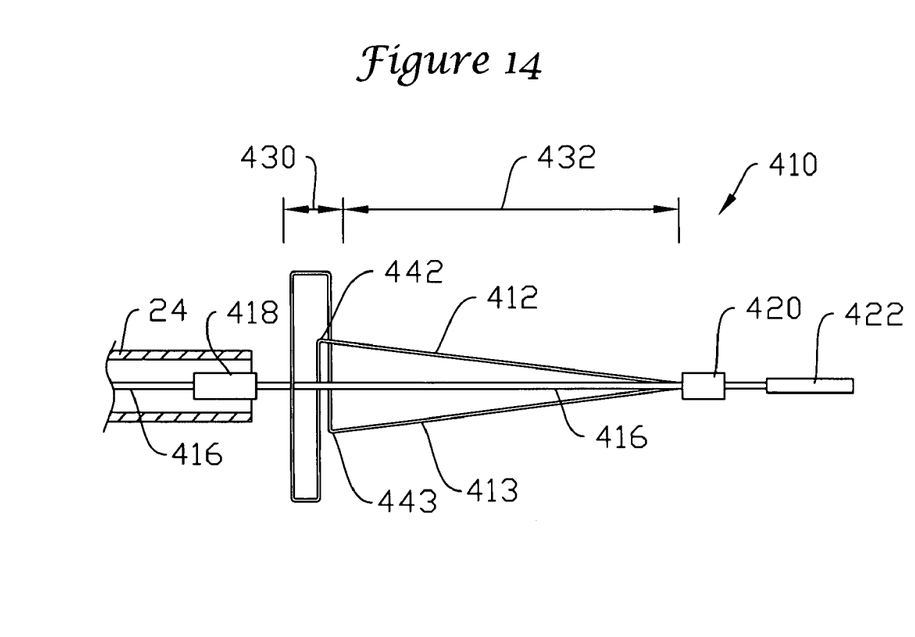
FIG. 14 is a top view of yet another alternate embodiment of an embolus extractor.

FIG. 14 is a top view of yet another alternate embodiment of an embolus extractor 410 in an expanded position. Embolus extractor 410 can be made from materials similar to, and used in a manner similar to embolus extractor 10 as described above. Embolus extractor 410 includes primary struts 412 and 413. Primary struts 412 and 413 can be coupled to an elongate shaft 416 at their proximal ends by sleeve 418 and at their distal ends by sleeve 420. Sleeve 418 or sleeve 420 can be slidable along shaft 416. It may be desirable, however, if both sleeve 418 and 420 are slidable along shaft 416 to provide a stop proximal sleeve 418. A distal spring tip 422 can act as a distal stop. Proximal portion 430 of primary struts 412 and 413 can form a generally circular mouth. Distal portion 432 of primary struts 412 and 413 can taper distally to form a generally tapered body. A transition between proximal portion 430 and distal portion 432 can occur at bend 442 along primary strut 412 and at bend 443 along primary strut 413.

Figure 15:
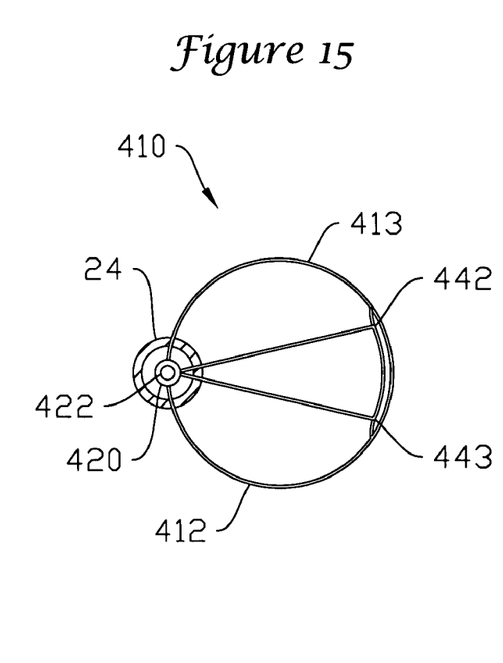
FIG. 15 is a distal end view of the embolus extractor of FIG. 14.

FIG. 15 is a distal end view of embolus extractor 410. The circular mouth and tapered body defined by struts 412 and 413 can be seen in FIG. 15. Additionally, it can be seen that strut 413 in part overlaps strut 412.

It should be understood that this disclosure is, in many respects, only illustrative. Changes may be made in details, particularly in matters of shape, size, and arrangement of steps without exceeding the scope of the invention. The inventor's scope is, of course, defined in the language in which the pending claims are expressed.

We claim:

1. An embolus extractor, comprising:
   an elongate shaft having a proximal end and a distal end;
   first and second struts, each strut having a proximal end coupled to the shaft and a distal end coupled to the distal end of the shaft, the struts having a first position and a second position;
   wherein in the first position, the distal ends and the proximal ends of the struts are spaced at a first distance, and in the second position the distal ends and the proximal ends of the struts are spaced at a second distance, the second distance being less than the first distance, and wherein in the second position the proximal ends of the struts form an open, generally circular mouth that is eccentric with respect to the shaft; and
   wherein the stuts can rotate about the elongate shaft.

2. An embolus extractor in accordance with claim 1, further comprising a sleeve slidably coupling the distal ends of the struts to the shaft.

3. An embolus extractor in accordance with claim 1, further comprising a sleeve slidably coupling the proximal ends of the struts to the shaft.

4. An embolus extractor in accordance with claim 1, wherein in the first position, the struts are disposed generally parallel to and adjacent the shaft.

5. An embolus extractor in accordance with claim 1, wherein the struts extend generally distally from the mouth to define a generally distally tapering body.

6. An embolus extractor in accordance with claim 1, wherein the proximal portion of the struts forming the mouth extend from the shaft at an angle of between 45° to 90° relative to the length of the shaft.

7. An embolus extractor in accordance with claim 6, wherein the proximal portions of the struts forming the mouth extend from the shaft at an angle of between 60° to 90° relative to the length of the shaft.

8. An embolus extractor in accordance with claim 7, wherein the proximal portions of the struts forming the mouth extend from the shaft at an angle of between 80° to 90° relative to the length of the shaft.

9. An embolus extractor in accordance with claim 1, wherein the struts include a shape memory metal.

10. An embolus extractor in accordance with claim 9, wherein the shape memory metal includes a NiTi alloy.

11. An embolus extractor in accordance with claim 1, further comprising a third strut coupled to the shaft, the third strut having a transverse cross sectional area; wherein the first and second struts each have a transverse cross sectional area greater than the transverse cross sectional area of the third strut.

12. The embolus extractor in accordance with claim 1, wherein the first and second struts can move independently of each other.

13. The embolus extractor in accordance with claim 1, wherein the struts can translate at least in part along the elongate shaft.

14. The embolus extractor in accordance with claim 1, wherein at least one strut includes a radiopaque material.

15. An embolus extractor in accordance with claim 16, wherein in the first position, the first strut is disposed generally parallel to the shaft.

16. An embolus extractor, comprising:
   an elongate shaft having a proximal end and a distal end;
   a first strut having a proximal end and a distal end, the proximal end and the distal end of the strut being coupled to the shaft, the strut having a first position and a second position;
   wherein in the first position, the distal end and the proximal end of the first strut are spaced at a first distance, and in the second position, the distal end and the proximal end of the first strut are spaced at a second distance being less than the first distance, and wherein in the second position, a proximal length of the first strut defines an open, generally circular mouth that is eccentric with respect to the shaft; and
   a second strut coupled to the shaft, the second strut having a transverse cross sectional area;
   wherein the first strut has a transverse cross sectional area greater than the cross sectional area of the second strut.

17. An embolus extractor in accordance with claim 16, wherein the first strut extends generally distally from the mouth to define a generally distally tapering body.

18. An embolus extractor in accordance with claim 16, wherein the proximal portion of the first strut forming the mouth extends from the shaft at an angle of between 45° and 90° relative to the length of the shaft.

19. An embolus extractor in accordance with claim 18, wherein the proximal portion of the first strut forming the mouth, extends from the shaft at an angle of between 60° and 90° relative to the length of the shaft.

20. An embolus extractor in accordance with claim 19, wherein the proximal portion of the first strut forming the mouth extends from the shaft at an angle of between 80° and 90° relative to the length of the shaft.

21. An embolus extractor in accordance with claim 16, wherein the first strut includes a shape memory metal.

22. An embolus extractor in accordance with claim 21, wherein the shape memory metal includes a NiTi alloy.

23. An embolus extractor, comprising:
   an elongate shaft having a proximal end and a distal end;
   first and second struts, each strut having a proximal end coupled to the shaft and a distal end coupled to the distal end of the shaft, the struts having a first position and a second position; and
   a sleeve slidably coupling the proximal ends of the struts to the shaft such that the struts can translate at least in part along the elongate shaft;
   wherein in the first position, the distal ends and the proximal ends of the struts are spaced at a first distance, and in the second position the distal ends and the proximal ends of the struts are spaced at a second distance, the second distance being less than the first distance, and wherein in the second position the proximal ends of the struts form an open, generally circular mouth that is eccentric with respect to the shaft.

24. The embolus extractor of claim 23, further comprising a sleeve slidably coupling the distal ends of the struts to the shaft.

25. An embolus extractor, comprising:
   an elongate shaft having a proximal end and a distal end;
   first and second struts, each strut having a proximal end coupled to the shaft and a distal end coupled to the distal end of the shaft, the struts having a first position and a second position; and
   a sleeve slidably coupling the distal ends of the struts to the shaft such that the struts can translate at least in part along the elongate shaft;
   wherein in the first position, the distal ends and the proximal ends of the struts are spaced at a first distance, and in the second position the distal ends and the proximal ends of the struts are spaced at a second distance, the second distance being less than the first distance, and wherein in the second position the proximal ends of the struts form an open, generally circular mouth that is eccentric with respect to the shaft.

* * * * *

UNITED STATES PATENT AND TRADEMARK OFFICE
CERTIFICATE OF CORRECTION

PATENT NO.        : 7,052,500 B2                                            Page 1 of 1
APPLICATION NO. : 10/045565
DATED             : May 30, 2006
INVENTOR(S)       : Mehran Bashiri et al.

It is certified that error appears in the above-identified patent and that said Letters Patent is hereby corrected as shown below:

Column 5, Line 61, delete "stuts" and add --struts--

Signed and Sealed this

Twelfth Day of December, 2006

JON W. DUDAS
*Director of the United States Patent and Trademark Office*